US010213099B2

(12) United States Patent
Bajramovic et al.

(10) Patent No.: US 10,213,099 B2
(45) Date of Patent: Feb. 26, 2019

(54) METHOD FOR PRODUCING OCT IMAGES AND OTHER IMAGES OF AN EYE INCLUDING REDUCING THE INTENSITY OF REFLECTED LIGHT

(71) Applicant: CARL ZEISS MEDITEC AG, Jena (DE)

(72) Inventors: Ferid Bajramovic, Jena (DE); Ralf Ebersbach, Schmölln (DE); Stephan Laqua, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 51 days.

(21) Appl. No.: 14/431,627

(22) PCT Filed: Sep. 27, 2013

(86) PCT No.: PCT/EP2013/070198
§ 371 (c)(1),
(2) Date: Mar. 26, 2015

(87) PCT Pub. No.: WO2014/049123
PCT Pub. Date: Apr. 3, 2014

(65) Prior Publication Data
US 2015/0257641 A1    Sep. 17, 2015

(30) Foreign Application Priority Data

Sep. 28, 2012  (DE) .................. 10 2012 019 469

(51) Int. Cl.
*A61B 3/10*   (2006.01)
*A61B 3/12*   (2006.01)
*A61B 3/14*   (2006.01)

(52) U.S. Cl.
CPC ............... *A61B 3/102* (2013.01); *A61B 3/12* (2013.01); *A61B 3/14* (2013.01)

(58) Field of Classification Search
CPC .. A61B 3/102; A61B 3/12; A61B 3/14; A61B 3/1015; A61B 3/103; A61B 3/032; A61B 3/107; G02C 1/02
(Continued)

(56) References Cited

U.S. PATENT DOCUMENTS

| 6,769,769 B2 * | 8/2004 | Podoleanu ............. A61B 3/102 351/221 |
| 7,706,862 B2 * | 4/2010 | Alfano ................. A61B 5/0059 600/310 |

(Continued)

FOREIGN PATENT DOCUMENTS

DE    10 2009 017 144 A1    10/2010

OTHER PUBLICATIONS

Notification of transmittal of Translation o the International Preliminary Report on Patentability for International Application No. PCT/EP2013/070198, dated Apr. 9, 2015, 8 pages.

(Continued)

*Primary Examiner* — William R Alexander
*Assistant Examiner* — Henry A Duong
(74) *Attorney, Agent, or Firm* — Patterson Thuente Pedersen, P.A.

(57) ABSTRACT

A method for measuring the geometric parameters of the eye. These measurements, known by the term biometrics, are particularly significant for the calculation of intraocular lenses after previous refractive cornea surgery. OCT images and other images are recorded simultaneously, the intensity of the reflected light generated during the OCT image recordings being lower by a factor of 2, by a factor of 10 or by a factor of 100, than the intensity of the illumination light of the other image recordings. The solution provides a method for producing other image recordings, in addition to OCT recordings, in the form of representations of the sclera (Continued)

or of the fundus, or keratometric, topographic or biometric measurements, or even short image sequences, for instance, while aligning the device with the eye.

18 Claims, 3 Drawing Sheets

(58) Field of Classification Search
USPC .......................................................... 351/246
See application file for complete search history.

(56) References Cited

U.S. PATENT DOCUMENTS

| | | | |
|---|---|---|---|
| 8,237,835 B1* | 8/2012 | Muller ........................ | 250/201.9 |
| 2004/0066489 A1* | 4/2004 | Benedikt ................ | A61B 3/107 |
| | | | 351/212 |
| 2005/0018137 A1 | 1/2005 | Barth et al. | |
| 2005/0109958 A1* | 5/2005 | Vernon ................... | G01T 1/172 |
| | | | 250/526 |
| 2005/0203422 A1 | 9/2005 | Wei | |
| 2006/0164653 A1* | 7/2006 | Everett ................. | A61B 3/102 |
| | | | 356/479 |
| 2008/0100612 A1* | 5/2008 | Dastmalchi ........... | G06F 19/321 |
| | | | 345/418 |
| 2010/0228119 A1* | 9/2010 | Brennan .............. | A61B 5/0066 |
| | | | 600/424 |
| 2010/0271594 A1 | 10/2010 | Bergner et al. | |
| 2011/0043661 A1 | 2/2011 | Podoleanu | |
| 2011/0051086 A1* | 3/2011 | Takai ....................... | A61B 3/12 |
| | | | 351/206 |
| 2011/0090325 A1* | 4/2011 | Hauger ................ | A61B 5/0261 |
| | | | 348/77 |
| 2011/0222020 A1* | 9/2011 | Izatt ....................... | A61B 3/102 |
| | | | 351/205 |
| 2012/0033227 A1* | 2/2012 | Bower ................... | A61B 3/102 |
| | | | 356/479 |
| 2012/0184846 A1* | 7/2012 | Izatt ................... | G02B 21/0012 |
| | | | 600/425 |
| 2013/0103014 A1* | 4/2013 | Gooding ................ | A61B 3/102 |
| | | | 606/6 |
| 2013/0194581 A1* | 8/2013 | Yoshida ............... | G01B 9/0203 |
| | | | 356/479 |

OTHER PUBLICATIONS

PCT International Search Report with English translation for PCT/EP2013/070198, dated Jul. 1, 2014, 5 pgs.
DE Search Report (5 Pgs.) with English translation (6 Pgs.) for DE 10 2012 019 469.2, dated Apr. 15, 2013.
Angela Baumgartner, et al., "Signal and Resolution Enhancements in Dual Beam Optical Coherence Tomography of the Human Eye", *Journal of Biomedical Optics* 3(1), 45-54 (Jan. 1998), 10 pgs.
ISO/CD 19980, "Ophthalmic instruments—Corneal topographers." 2009, 31 pages.
English preview summarizing ISO/CD 19980, "Ophthalmic instruments—Corneal topographers." 2009, 9 pages.

* cited by examiner

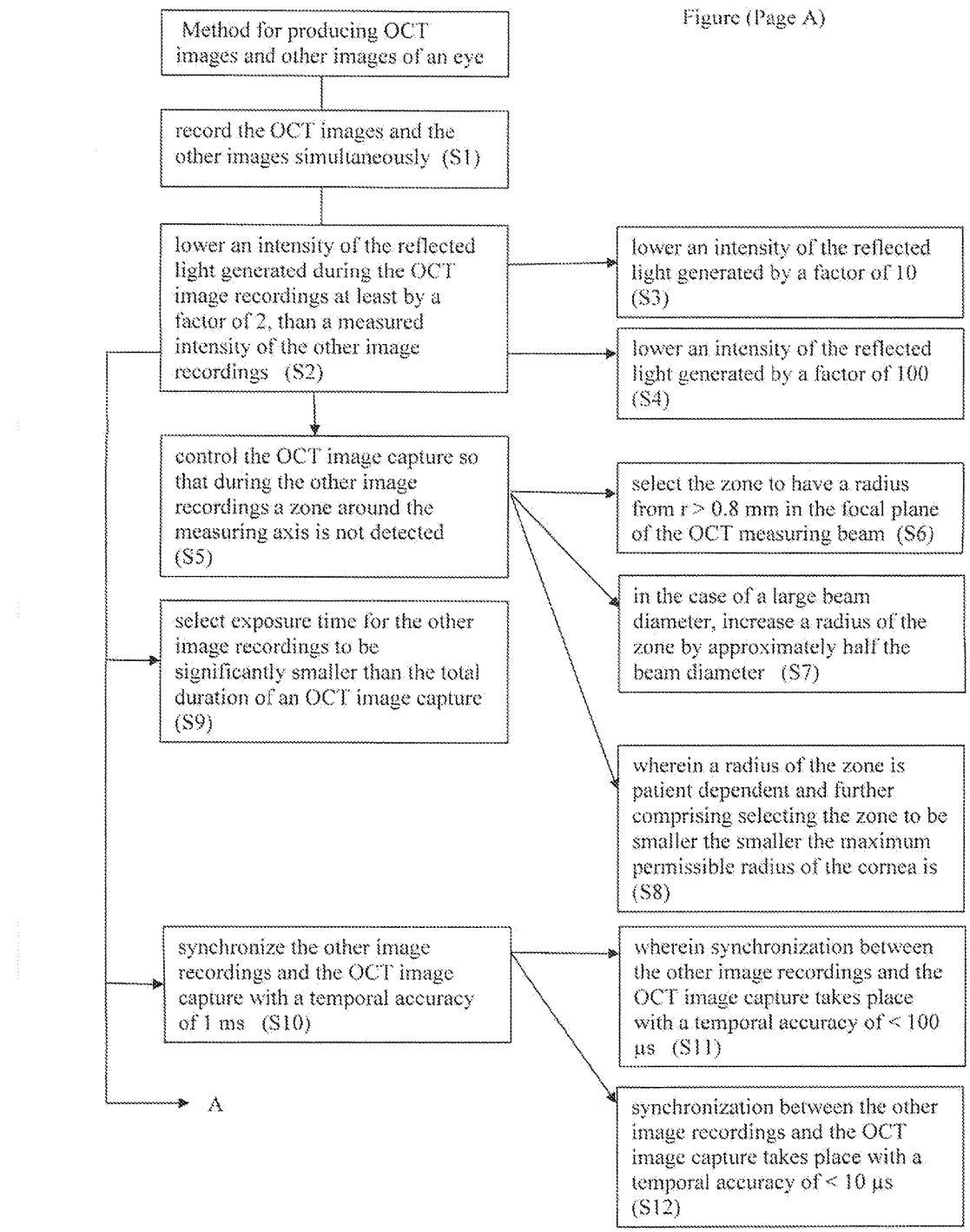
Figure (Page A)

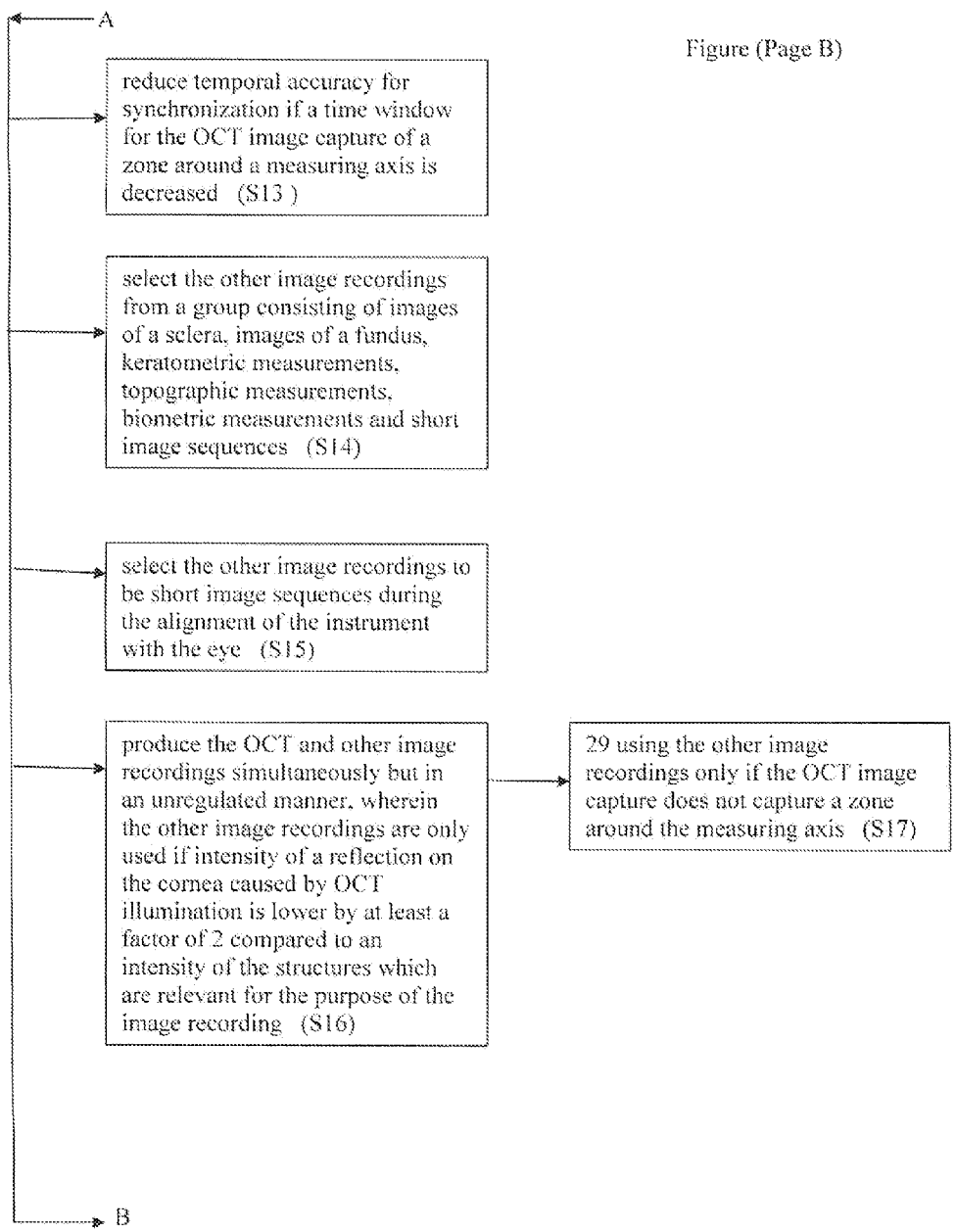

Figure (Page C)

produce the OCT and other image recordings simultaneously but in an unregulated manner, wherein the other image recordings are only used if intensity of a reflection on the cornea caused by OCT illumination is lower by at least a factor of 10 compared to an intensity of the structures which are relevant for the purpose of the image recording (S18)

produce the OCT and other image recordings simultaneously but in an unregulated manner, wherein the other image recordings are only used if intensity of a reflection on the cornea caused by OCT illumination is lower by at least a factor of 100 compared to an intensity of the structures which are relevant for the purpose of the image recording (S19)

METHOD FOR PRODUCING OCT IMAGES AND OTHER IMAGES OF AN EYE INCLUDING REDUCING THE INTENSITY OF REFLECTED LIGHT

RELATED APPLICATIONS

The present application is a National Phase entry of PCT Application No. PCT/EP2013/070198, filed Sep. 27, 2013, which claims priority from DE Patent Application No. 10 2012 019 469.2, filed Sep. 28, 2012, said applications being hereby incorporated by reference herein in their entirety.

FIELD OF THE INVENTION

The present invention relates to a method for producing OCT images and other images of an eye, from which images the geometric parameters of the eye can be determined. These measurements, known by the term biometrics, are particularly significant for the calculation of intraocular lenses after previous refractive cornea surgery.

BACKGROUND

Numerous solutions for this purpose are known according to the prior art. For highly precise axial length measurement, solutions which are based on methods of optical coherence tomography (OCT), partial coherence interferometry (PCI) or the like have become established in the prior art.

The basic principle of the OCT method is based on white light interferometry and compares the propagation time of a signal with the aid of an interferometer (generally a Michelson interferometer). The arm with a known optical path length (=reference arm) is used as a reference for the measurement arm. The interference of the signals from both arms produces a pattern from which the relative optical path length within an A-scan (single depth signal) can be read out. In the one-dimensional scanning grid methods the beam is then guided, as in ultrasound technology, transversely in one or two directions, so that a two-dimensional B-scan or a three-dimensional tomogram (C-scan) can be recorded. In this case the amplitude values of the individual A-scans are typically represented in logarithmized grey-scale or pseudo-colour values.

If further measurement variables are required in addition to the axial length (AL), central radii of front of the cornea (K), anterior chamber depth (ACD) and limbus diameter (WTW), these further variables may be determined for example from keratometric or topographical image recordings of the eye.

Although these further measurement variables and the OCT measured values are measured by different instruments, the integration of the measurement both of the OCT and also of the further measurement variables in one instrument facilitates simpler handling, for example only one single alignment of the instrument with the patient and an improved lateral registration of the OCT measured values with the further measured values.

However, in a combined instrument the different measurement modalities should not influence one another during the measurement. An influence may be specifically manifested in that light from the OCT measuring system can be seen in one or more images of the other measuring system for example as a bright spot, which can disrupt the measurement. In order to ensure this absence of influence 2 groups of solutions are possible:

In a first group of solutions the different recordings are made sequentially, i.e. one after the other.

One example is shown in US 2005/0203422 A1, which shows a combined system comprising keratometer and OCT tomography. In order to separate the two modalities from one another, a chronological separation is likewise proposed here.

A further example is the IOLMaster from Carl Zeiss. This is a combined instrument which determines the keratometry, the axial length by means of PCI (partial coherence interferometry) and the anterior chamber depth by means of slit-lamp illumination and image detection, as well as further parameters of the eye such as the so-called white-to-white-distance.

With all these measurements which take place sequentially the time spent on the measurements is longer. Moreover, it is disadvantageous that the different measurements of OCT and ultrasound and/or keratometry could take place on the basis of possible eye movements at slightly different places. In general, therefore, a reproducibility of the measurement is accordingly difficult to achieve.

In a second group of solutions, the different recordings are made simultaneously, for which the measurement systems must have a corresponding optical separation.

As a further example, in US 2005/0018137 A1 a combined system comprising keratometer and axial length measurement by means of PCI is described. In this case the separation of both modalities is achieved by beam splitting by means of polarization separation.

The above-mentioned US 2005/0203422 A1 also mentions, as an alternative to the sequential measurement of the modalities (by means of OCT and keratometry), a separation of the modalities by a dichroitic beam splitter.

In all these examples an optical separation of the different measurement systems takes place either by the use of different wavelengths or by means of additional optical elements which prevent the measurement systems from influencing one another.

This is disadvantageous in such systems in that correspondingly higher demands are made on the optics and/or camera, which can have a negative effect on the producibility and/or price level thereof.

SUMMARY OF THE INVENTION

The present invention includes a method for producing OCT images and other images of an eye, which method enables the simultaneous production of OCT images and other images without illuminating light from the other measuring systems disrupting the images or the measurement.

The object is achieved by the method according to the invention for producing OCT images and other images of an eye, in that OCT images and other images are recorded simultaneously, the intensity of the reflected light generated during the OCT image recordings being lower, for example by at least a factor of 2, in another example by a factor of 10, and in a further example by a factor of 100, than the measured intensity of the other image recordings.

The present solution provides a method for implementation of image recordings of an eye, by which method in addition to OCT recordings other image recordings in the form of images of the sclera or of the fundus, or keratometric, topographic or biometric measurements, or even short image sequences can be made for example during the alignment of the instrument with the eye.

The invention is described in greater detail below with reference to embodiments.

BRIEF DESCRIPTION OF THE DRAWINGS

The FIGURE depicts a flowchart of an example method according to the invention.

DETAILED DESCRIPTION

In the method according to the invention for producing OCT and other image recordings, the OCT images and other images are recorded simultaneously S1, the intensity of the reflected light generated during the OCT image recordings being lower at least by a factor for example of 2 S2, in another example by a factor of 10 S3 and in another example by a factor of 100 S4, than the intensity of the illumination light for the other image recordings.

According to the invention a non-strict separation is provided between OCT image recordings and other image recordings. For this purpose OCT measurements and the other image recordings are made so that they overlap in time in such a way that the other image recording is made when the beam of light from the OCT measurement lies on the object or the interfaces in the object in such a way that the reflections thereof on the object are small enough relative to the actual image signals so as not to falsify the image signal. Conversely the other image recordings then do not take place or are not used for a further evaluation if the OCT illumination impinges approximately perpendicularly onto the surface of the cornea.

In particular in the method according to the invention the OCT image capture is controlled so that during the other image recordings a zone around the measuring axis of the ophthalmological instrument is not illuminated or captured by the OCT S5. If the ophthalmological instrument is aligned exactly with the eye to be examined, the measuring axis extends through the vertex of the cornea according to the bibliography [1].

In the case where scanners are used for the OCT image capture in order to capture two-dimensional B-scans or three-dimensional volume scans, these scanners are controlled so that during the exposure time for the other image recordings the zone around the measuring axis is not scanned by the scanners.

On the other hand, if the OCT image capture takes place merely in the form of A-scans or if the above-mentioned deliberate control of the scanner is omitted, the use of illumination sources which can be activated and deactivated suitably quickly is sufficient. Even from laser sources activation and deactivation times of <2 µs are achieved.

Experience shows that the zone around the measuring axis for example has a radius from r>0.8 mm in the focal plane of the OCT measuring beam S6. In the case of a large beam diameter the radius of the zone may be increased by approximately half the beam diameter S7.

Moreover the radius of the zone depends upon the patient, so that it can be selected to be smaller the smaller the maximum permissible radius of the cornea is S8.

In this connection it should be noted that eye movements during the exposure time of the other image recordings, for typical recording times of 4 ms, in any case only have an insignificant effect.

Vertex movements to be typically expected during an exposure time of 4 ms amount to approximately 1 mm/s at 4 µm for an average eye movement and are therefore insignificant.

Eye movements are relevant for longer exposure times. Since the vertex of the cornea then moves, the above-mentioned zone should be correspondingly enlarged.

According to a further exposure time of the method according to the invention the exposure time for the other image recordings is for example significantly smaller than the total duration of an OCT image capture S9.

Thus, for example, with an exposure time for the other image recordings of 4 ms and an image repetition rate of 20 images per second for the OCT image capture a time window of 46 ms remains in which the OCT image capture of the zone around the measuring axis can take place. If a nominal lateral resolution of the OCT of less than 20 µm is to be achieved in this zone of for example 0.8 mm radius, the A-scan must take place at a frequency of greater than 1740 Hz.

$$f > 2 \times 0.8 \text{ mm}/20 \text{ µm} \times 46 \text{ ms} \qquad (1)$$

According to a further embodiment of the method according to the invention, the synchronization necessary for this takes place between the other image recording and the OCT image capture with a temporal accuracy for example <1 ms S10, in another example <100 µs S11 and in a further example of <10 µs S12.

However, these requirements relating to temporal accuracy for the synchronization may be reduced if the time window for the OCT image capture of the zone around the measuring axis is decreased, i.e. if a time buffer is provided before and after the exposure time for the other image recordings S13.

In this connection it should be noted that the requirement relating to temporal accuracy for the synchronization is dependent on different factors, such as for example the image repetition rate, the exposure time, scanning rate, settling behavior of the scanner inter alia.

Furthermore is should also be noted that by the use of software and/or hardware the control can be optimized so that in principle significantly higher temporal accuracy can be achieved.

Alternatively or as a complement to the embodiments described above with regard to control of the OCT image recordings and the other image recordings, the OCT image recordings and the other image recordings can also take place simultaneously but in an unregulated manner with respect to one another S16. However, for the further analysis of the image recordings, such as for example for determination of the keratometer values from the image recording, only those image recordings are used in which the intensity of the reflection on the cornea caused by the OCT illumination is lower for example by at least a factor of 2 S16, in another example by a factor of 10 S18, in a further example by a factor of 100 S19, than the intensity of the structures in the other image recording which are relevant for the purpose of the image recording.

Then, for example, only those image recordings in which the OCT scan does not lie in the zone described above around the measuring axis are used for the further analysis of the image recordings S17.

According to a final embodiment of the method according to the invention, the other image recordings may be images of the sclera or fundus, or keratometric, topographic or biometric measurements or even short image sequences S14, for example during the alignment of the instrument with the eye S15.

All possible camera-based measurements and recordings which are produced according to the method proposed here simultaneously with the OCT image recordings are conceivable in principle.

The solution according to the invention provides a method for producing image recordings of an eye, by which method in addition to OCT recordings other image recordings in the form of images of the sclera or of the fundus, or keratometric, topographic or biometric images can be made.

The proposed method effectively prevents the image capture from optical coherence tomography OCT and other image recordings from influencing one another, so that the measurements are not disrupted.

This does not necessitate increased expenditure on equipment nor setting of higher standards for the optics and/or camera, which can have a negative effect on the producibility and/or price level thereof.

Due to the simultaneous production of OCT image recordings and other image recordings the influence of eye movements is less than in the case of sequential recordings and thus the reproducibility is generally better.

Bibliography:

[1] ISO/CD 19980, "Ophthalmic instruments—Corneal topographers." 2009

The invention claimed is:

1. A method for producing OCT images and other images of an eye, comprising:
   in preparation for intraocular lens implant surgery recording the OCT images and the other images of the eye simultaneously to create OCT image recordings and other image recordings captured while the eye is in a similar position;
   recording the other images of anatomical structures of the eye or relating to biometric, keratometric or topographic measurements of the anatomical structures;
   measuring an intensity of the other image recordings; and
   lowering an intensity of reflected light reflected from the eye generated during the OCT image recordings at least by a factor of 2, as compared to the measured intensity of the other image recordings by adjustment of an illumination source or adjustment of image capture optical elements.

2. The method according to claim 1, further comprising lowering an intensity of the reflected light generated during the OCT image recordings by a factor of 10 compared to the measured intensity of the other image recordings.

3. The method according to claim 1, further comprising lowering an intensity of the reflected light generated during the OCT image recordings by a factor of 100 compared to the measured intensity of the other image recordings.

4. The method according to claim 1, further comprising controlling the OCT image capture so that during the other image recordings a zone around a measuring axis is not detected.

5. The method according to claim 4, further comprising selecting the zone to have a radius from r>0.8 mm in the focal plane of the OCT measuring beam.

6. The method according to claim 4, further comprising, in the case of a large beam diameter, increasing a radius of the zone by approximately half the large beam diameter.

7. The method according to claim 4, wherein a radius of the zone is patient dependent and further comprising selecting the zone to be smaller when a maximum permissible radius of the cornea is smaller.

8. The method according to claim 1, further comprising selecting exposure time for the other image recordings to be significantly smaller than the total duration of an OCT image capture.

9. The method according to claim 1, further comprising synchronizing the other image recordings and the OCT image capture with a temporal accuracy of 1 ms.

10. The method according to claim 9, wherein synchronization between the other image recordings and the OCT image capture takes place with a temporal accuracy of <100 µs.

11. The method according to claim 9, wherein synchronization between the other image recordings and the OCT image capture takes place with a temporal accuracy of <10 µs.

12. The method according to claim 1, further comprising reducing temporal accuracy for synchronization if a time window for the OCT image capture of a zone around a measuring axis is decreased.

13. The method according to claim 1, further comprising selecting the other image recordings from a group consisting of images of a sclera, images of a fundus, keratometric measurements, topographic measurements, biometric measurements and short image sequences.

14. The method according to claim 1, further comprising selecting the other image recordings to be short image sequences during the alignment of the instrument with the eye.

15. The method according to claim 1, further comprising producing the OCT and other image recordings simultaneously but in an unregulated manner, wherein the other image recordings are only used if intensity of a reflection on the cornea caused by OCT illumination is lower by at least a factor of 2 compared to an intensity of the structures which are relevant for the purpose of the image recording.

16. The method according to claim 15, further comprising using the other image recordings only if the OCT image capture does not capture a zone around the measuring axis.

17. The method according to claim 1, further comprising producing the OCT and other image recordings simultaneously but in an unregulated manner, wherein the other image recordings are only used if intensity of a reflection on the cornea caused by OCT illumination is lower by at least a factor of 10 compared to an intensity of the structures which are relevant for the purpose of the image recording.

18. The method according to claim 1, further comprising producing the OCT and other image recordings simultaneously but in an unregulated manner, wherein the other image recordings are only used if intensity of a reflection on the cornea caused by OCT illumination is lower by at least a factor of 100 compared to an intensity of the structures which are relevant for the purpose of the image recording.

* * * * *

UNITED STATES PATENT AND TRADEMARK OFFICE
CERTIFICATE OF CORRECTION

PATENT NO. : 10,213,099 B2
APPLICATION NO. : 14/431627
DATED : February 26, 2019
INVENTOR(S) : Ferid Bajramovic et al.

It is certified that error appears in the above-identified patent and that said Letters Patent is hereby corrected as shown below:

In the Specification

Column 1, Line 67, delete "possible:" and insert --possible.--

Column 3, Line 4, delete "DRAWINGS" and insert --DRAWING--

Signed and Sealed this
Fourteenth Day of April, 2020

Andrei Iancu
*Director of the United States Patent and Trademark Office*